United States Patent [19]

Murao et al.

[11] Patent Number: 4,732,857

[45] Date of Patent: Mar. 22, 1988

[54] PROCESS FOR PRODUCING ENZYME CAPABLE OF INACTIVATING CYTOSOLIC ASPARTATE AMINOTRANSFERASE ISOZYME

[76] Inventors: Sawao Murao, 8-12, Horiagemidori-machi 2-cho, Sakai-shi, Osaka; Toyokazu Nishino, 15-1, Ueno-cho, Ibaragi-shi, Osaka, both of Japan

[21] Appl. No.: 688,251

[22] Filed: Jan. 2, 1985

[30] Foreign Application Priority Data

Jan. 12, 1984 [JP] Japan ................................. 59-4494

[51] Int. Cl.[4] .......................... C12N 9/52; C12R 1/465
[52] U.S. Cl. ..................................... 435/220; 435/886
[58] Field of Search .............. 435/68, 193, 253, 886, 435/69, 220

[56] References Cited

U.S. PATENT DOCUMENTS 4,477,566  10/1984  Ricci et al. ........................... 435/16

OTHER PUBLICATIONS

Murao et al.; 'Cytosolic Aspartate Aminotransferase Inactivating-enzyme from *Streptomyces violaceochromogenes*'; *Agric. Biol. Chem.*, vol. 48, No. 8, Aug. 1984, pp. 2163–2166.

*Primary Examiner*—Elizabeth Weimar
*Attorney, Agent, or Firm*—Wegner & Bretschneider

[57] ABSTRACT

A process for preparing an enzyme capable of inactivating cytosolic aspartate aminotransferase isozyme. The process comprises cultivating a strain of *Streptomyces violaceochromogenes* species capable of producing said enzyme to produce and accumulate said enzyme and recovering said enzyme from the culture.

1 Claim, 2 Drawing Figures

PROCESS FOR PRODUCING ENZYME CAPABLE OF INACTIVATING CYTOSOLIC ASPARTATE AMINOTRANSFERASE ISOZYME

BACKGROUND OF THE INVENTION

1. Field of the Invention

The present invention relates to a process for preparing an enzyme capable of inactivating cytosolic aspartate aminotransferase (EC 2.6.1.1, systematic name=L-Aspartate: 2-oxoglutarate aminotransferase; another name=glutamic-oxaloacetic transaminase; hereinafter referred to as "AST") isozyme, by cultivating a strain of genus Streptomyces.

2. Description of the Prior Art

AST isozymes occur in the liver, myocardium, brain, skeletal muscle, kidney and the like, and have been known as enzymes which catalyze the following reaction:

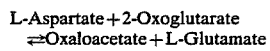

$$\text{L-Aspartate} + \text{2-Oxoglutarate} \rightleftharpoons \text{Oxaloacetate} + \text{L-Glutamate}$$

The AST isozymes include two kinds of isozymes different in localization, one being a cytosolic AST isozyme (hereinafter referred to as "s-AST") and the other a mitochondrial AST isozyme (hereinafter referred to as "m-AST"). Fractional determination of these isozymes is useful for the clinical diagnosis of hepatitis, myocardial infarction, etc.

On the susceptibility of AST isozymes to proteases, there are reports by E. Sandmeier et al. (J. Biol. Chem., Vol. 255, 10284–10289 (1980)) and by D. E. Metzler et al., (Federation Proceedings, Vol. 41, 2432–2436 (1982)). E. Sandmeier et al. have reported that trypsin limitedly cleaved m-AST to inactivate it, and in a preliminary experiment a similar proteolytic cleavage of s-AST was observed. D. E. Metzler et al. have described that m-AST was inactivated by trypsin though more slowly than s-AST.

SUMMARY OF THE INVENTION

For the purpose of achieving the fractional determinations of AST isozymes, the present inventors searched for substances inhibiting the activity of one of these isozymes. It has been revealed that a strain of genus Streptomyces which was found in soil microorganisms by the present inventors produces a substance which inhibits s-AST but does not inhibit m-AST at all. Moreover, from the purification and isolation and the examination of physical and chemical properties, this substance has proved unexpectedly to be a proteolytic enzyme belonging to the serine protease group.

Accordingly, the present inventors are the first to discover an enzyme acting as a specific inhibitor to s-AST. Based on the above-finding, the present invention has been accomplished, and thus it has been confirmed that the s-AST-inactivating enzyme produced according to the process of the present invention is useful for the fractional determination of AST isozymes.

According to the invention, there is provided a process for preparing an enzyme capable of inactivating cytosolic aspartate aminotransferase isozyme which comprises cultivating a strain of *Streptomyces violaceochromogenes* species capable of producing said enzyme to produce and accumulate said enzyme and recovering said enzyme from the culture.

BRIEF DESCRIPTION OF THE DRAWINGS

Similarly

DETAILED DESCRIPTION OF THE PREFERRED EMBODIMENTS

Figure 1:
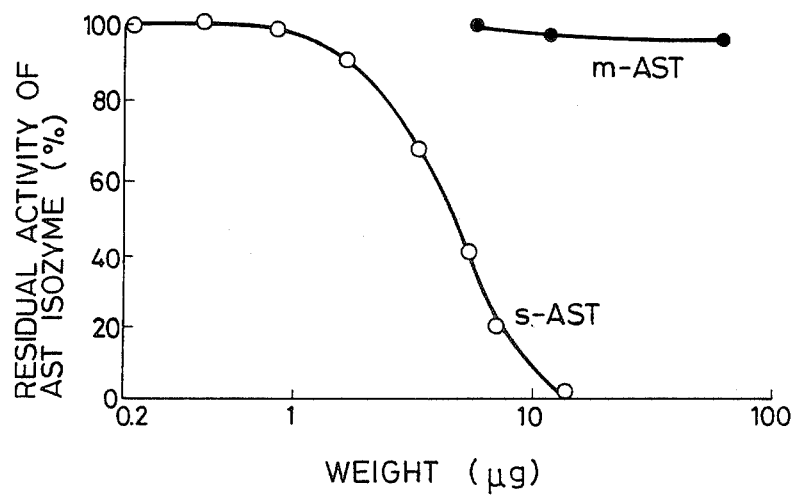
FIG. 1 shows the relationship between the dose (weight) of the s-AST-inactivating enzyme of the present invention and the AST isozyme inhibitory activities thereof.

While any strain of Streptomyces capable of producing the s-AST-inactivating enzyme may be used in the present invention, it is preferred to use the strain No. 9722 of Streptomyces that the present inventors found by screening strains isolated from soil. Mycological properties of the strain No. 9722 are described below:

(a) Morphology

Aerial hyphae of about 1μ in diameter extend from substrate hyphae and have open spiral chains of spores on the top. The aerial hyphae have simple branching and no verticillus. The spore is in elliptical or cylindrical form and with smooth surface. The number of spores in chains is at least 10. The size of the spore is 0.6–1.2μ×0.7–1.8μ. No hairy spore, sclerotium, and sporangium are observed.

(b) Growth in various medium

These are shown in Table 1 (cultivation periods 14–21 days).

TABLE 1

| Medium | Growth | Color of substrate mycelium (reverse color) | Aerial mycelium (amount, color) | Soluble pigment |
| --- | --- | --- | --- | --- |
| Sucrose-Nitrate agar | Good | Yellowish white | Rich, brown-gray | Deep red-purple |
| Glucose-Asparagine agar | Fair | Yellowish white | Ordinary, brown-gray | Light red-purple |
| Glycerol-Asparagine agar | Fair | Yellowish white | Ordinary, brown-gray | Red-purple |
| Inorganic salts-Starch agar | Good | Cream color | Rich, grayish olive | None |
| Tyrosine agar | Good | Dull red-purple | Rich, grayish olive | Deep red-purple |
| Nutrient agar | Good | Cream color | Rich, brown-gray | Yellowish Brown |
| Yeast extract-Malt extract agar | Fair | Cream color | Poor, light brown-gray | Yellowish Brown |
| Oatmeal agar | Fair | Yellowish white | Poor, light brown-gray | None |
| Peptone-Yeast extract Iron agar | Fair | Yellowish white | Ordinary, light brown-gray | Yellowish Brown |

(c) Physiological properties (i) Range of growth temperatures

The tests using a temperature-gradient incubator showed that the strain grew in the range of 10° to 36° C. in Bennett's broth.

(ii) Liquefaction of gelatin: positive (iii) Hydrolysis of starch: positive
(iv) Coagulation of skim milk: negative
(v) Peptonization of skim milk: positive
(vi) Formation of melanoid pigment: positive (d) Ability to assimilate carbon sources (on Pridham and Gottlieb carbon utilization medium)

D-glucose, D-xylose, L-arabinose, L-rhamnose, D-fructose, D-galactose, D-mannitol, salicin, and sucrose are utilized for growth. No growth or only trace of growth with inositol and raffinose.

The above noted properties of the strain No. 9722 are summarized as follows: The aerial hyphae form spirals, the spore surface is smooth, the color of the aerial mycelium is brown-gray or grayish olive, and the strain gives positive melanoid pigment production and yields soluble red-purple pigment in certain media. For information on strains having such mycological properties, there were consulted Bergey's Manual of Determinative Bacteriology, the 7th edition (1957), ibid., the 8th edition (1974), Shirling and Gottlieb ISP (International Sreptomyces Project) report (1968, 1969, and 1972), and "The actinomycetes" written by S. A. Waksman, Vol. 2 (1961). As a result, Streptomyces violaceochromogenes was found to be most close in nature to the strain No. 9722. That is, S. violaceochromogenes is in good agreement with the strain No. 9722 in that the aerial mycelium is grey in color and forms spirals, the strain forms soluble red-purple pigment, the spore surface is smooth, and the strain is positive in the production of melanoid pigment (positive in a peptone-yeast-iron agar medium and negative in a tyrosin agar medium). Referring to the assimilation of sugars S. violaceochromogenes is different from the strain No. 9722 in utilizing neither inositol nor raffinose.

The above slight difference in the utilization of sugars is not so significant that the strain No. 9722 and S. violaceochromogenes are considered to belong to different species. Accordingly, the strain No. 9722 was named S. violaceochromogenes No. 9722 and has been deposited as FERM BP-646 (Original Accession number: FERM P-7362) in Fermentation Research Institute, Agency of Industrial Science and Technology, of 1-3, Higashi 1-chome, Yatabe-machi, Tsukuba-gun, Ibaraki 305, Japan on Dec. 12, 1983, in conformance with Budapest Treaty on the International Recognition of the Deposit of Microorganisms for the Purposes of Patent Procedure.

For the preparation of the s-AST-inactivating enzyme according to the process of the present invention, a strain of Streptomyces producing the s-AST-inactivating enzyme is first cultivated in a nutrient medium to accumulate the enzyme in the culture. The cultivation can be carried out according to conventional methods for actinomycetes. For example, the nutrient medium contains carbon sources, nitrogen sources, and inorganic components which the microorganism can utilize. Suitable carbon sources include glucose, fructose, maltose, sucrose, molasses, starch, dextrin, organic acids, glycerol, etc. Suitable nitrogen sources include organic nitrogen sources, e.g. malt extract, peptone, yeast extract, dry yeast, meat extract, corn steep liquor, casein, and amino acids, and inorganic nitrogen sources, e.g. nitrates and ammonium salts. Suitable inorganic components include salts of potassium, sodium, magnesium, calcium, zinc, iron, and the like, which are used as required. An anti-foaming agent such as a surfactant, silicone, or vegetable oil may be added to suppress the foaming during incubation.

The cultivation is preferred to be carried out under aerobic conditions with shaking or agitating by aeration. The culture medium may be kept at any temperature where the strain grows and the s-AST-inactivating enzyme is produced, but preferably in the range of 20°-35° C. The desirable pH value of the culture medium is in the range of from 6 to 9. The cultivation period is selected so as to give a maximum yield of the enzyme at the end of the period. It is usually in the range of 30-50 hours.

From a thus obtained culture, the s-AST-inactivating enzyme of the present invention can be recovered by means of conventional protein purification techniques so as to utilize physical and chemical properties of the enzyme. For instance, after the cells have been removed from the culture broth by filtration or centrifugation, the enzyme is purified by known techniques such as: salting out by use of ammonium sulfate, sodium sulfate, or the like; precipitation with an organic solvent, e.g. ethanol, methanol, or acetone; adsorption chromatography with, e.g. activated carbon, silica gel, alumina, hydroxy-apatite, or cellulose; ion exchange chromatography with, e.g. ion exchange resin, ion exchange cellulose, or ion exchange Sephadex; gel filtration with, e.g. Sephadex or Bio-gel; and electrophoresis, ultrafiltration, and dialysis.

The s-AST-inactivating enzyme of the present invention has the following physical and chemical properties:

(1) Action: The enzyme inactivates s-AST but not m-AST. It catalyzes the hydrolysis of proteins such as casein.

(2) Substrate specificity on protein: The enzyme is active against casein, hemoglobin, azocoll, and albumin.

(3) Optimum pH for the casein-hydrolyzing activity: The optimum pH was about 11.6 as estimated in solutions of substrate casein (1.33%) in Tris-HCl buffers (pH 7-9) and in glycine-NaOH buffers (pH 10-12).

(4) pH Stability: After treatment at 37° C. for 14 hours the enzyme was stable in the pH range of 5 to 6.

(5) Optimum temperature for the casein-hydrolyzing activity: For the hydrolysis of casein at pH 9.5 for 10 minutes, the maximum activity of the enzyme was observed at 75° C.

(6) Thermal stability: Treatment at pH 8.5 for 10 minutes at different temperatures indicated that the enzyme retained 100% of the initial activity at 55° C. and 85% thereof at 65° C.

(7) Molecular weight: 17,500-18,000 (estimated by SDS polyacrylamide gel electrophoretic method).

(8) Isoelectric point: 9.8 (calculated from electrofocussing method).

(9) Inhibitor: The enzyme activity was inhibited by phenylmethylsulfonyl fluoride but not by EDTA.

(10) Color and crystal form: White rhombohedral crystals.

As described above, the s-AST-inactivating enzyme of the present invention is identified as a protease, more specifically a serine protease.

The s-AST inhibitory activity of the enzyme of the present invention was assayed as follows: 0.5 ml of the s-AST-inactivating enzyme solution prepared by the present invention is mixed with 0.5 ml of 50 mM Tris-HCl buffer (pH 8.5) containing s-AST (50 Karmen units, prepared from pig heart according to the method of Y. Morino et al., J. Biochem., 82, pp. 847-852, 1977), bovine serum albumin (0.1 mg/ml) and pyridoxal phosphate (4 $\mu$M). The reaction mixture is incubated at 25° C. for 15 minutes, and then mixed with 3.0 ml of 50 mM Tris-HCl buffer (pH 8.0) containing aspartic acid (20 mM), 2-oxoglutaric acid (10 mM), NADH (0.2 mM), and malate dehydrogenase (10 units; supplied by Oriental Yeast Co., Ltd.) to initiate the reaction at 25° C. The decrease in the absorbance at 340 nm per minute is measured. The absorption value thus found is compared with the value obtained by the above procedure but using water instead of the inactivating enzyme solution, and the inhibitory activity of the enzyme which reduces the absorbance to 50% of the latter value is defined as one unit.

Figure 2:
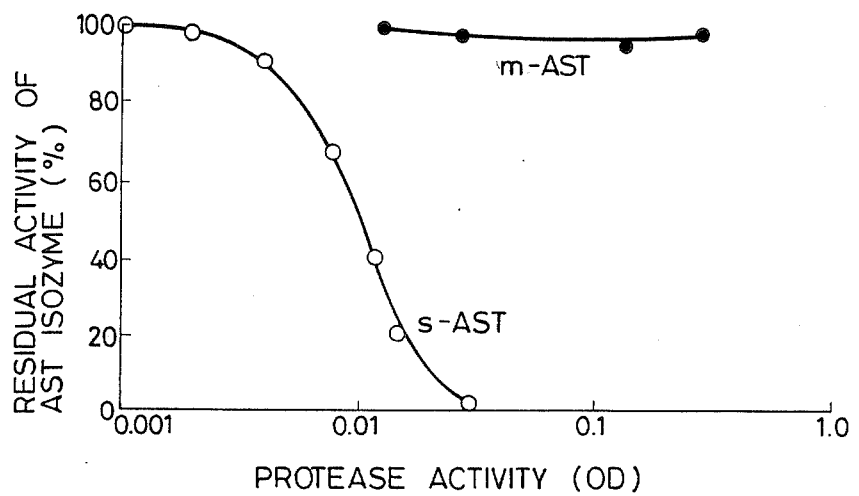
FIG. 2 shows the relationship between the protease activity of the enzyme and the AST isozyme inhibitory activities thereof.

An example of tests for the action of the inactivating enzyme of the present invention on AST isozymes is illustrated below. That is, residual activities of s-AST and m-AST (prepared according to the previous method for s-AST) were estimated by the above assay procedure of inhibitory activity but with varying quantities and protease activities of the inactivating enzyme. One unit of the protease activity herein is the optical density (OD) value determined by reacting the s-AST-inactivating enzyme with substrate casein at 37° C. for 10 minutes, adding Folin's reagent to the trichloroacetic acid-soluble fraction obtained, and measuring the absorbance at 660 nm of the resulting blue solution. From the results, as shown in FIGS. 1 and 2, the enzyme of the present invention has proved to inhibit s-AST but not m-AST at all.

The invention is illustrated in more detail with reference to the following example:

EXAMPLE

A loop of *Streptomyces violaceochromogenes* No. 9722 (FERM BP-646) from an agar slant culture was inoculated to 100 ml of medium (pH 7.0) comprising 1.0% glucose, 1.0% polypeptone, 1.0% meat extract, 0.3% sodium chloride, and 0.02% Adekanol (tradename of antifoaming agent supplied by Asahi Denka Co., Ltd.) in a 500-ml shaking flask. The culture was grown for 40 hours at 30° C. with reciprocal shaking to prepare a seed culture broth. A medium (18 l) of the same composition as in the above was charged in a 30-l jar fermenter, and the above seed culture was inoculated and grown at 28° C. under an inner pressure of 0.5 Kg/cm$^2$ for 40 hours with aeration (9 l/min.) and agitation (300 rpm).

The resulting culture broth was filtered to remove the cells, and the filtrate was 80% saturated with ammonium sulfate and left standing overnight. The resulting precipitate was collected by centrifugation, and dissolved in a 50 mM acetate buffer (pH 4.0). The solution was dialyzed against a buffer of the same composition by means of a cellophane tube. The dialyzed solution was charged on an SP-Sephadex C-50 (supplied by Pharmacia Fine Chemical Co.) column (4.8 cm$\phi\times$28 cm L), which had been pre-equilibrated with a buffer of the same composition before use, then eluted with 0–0.6 M NaCl gradient. The active fractions eluted with 0.25 to 0.3 M NaCl solution were collected and 80% saturated with ammonium sulfate. The resulting precipitate was collected by centrifugation, and dissolved in a 40 mM boric acid-KOH buffer (pH 9.7). This enzyme solution was dialyzed against a buffer of the same composition, and passed through a DEAE - Sephadex A-25(supplied by Pharmacia Fine Chemical Co.) column (2.0 cm$\phi\times$10 cm L) which had been pre-equilibrated with a buffer of the same composition before use. The enzyme weakly adsorbed on this resin was eluted by successive passage of the same buffer. Ammonium sulfate was dissolved in the eluate to 80% saturation, and the resulted precipitate was collected by centrifugation. The precipitate was dissolved in a 40 mM boric acid-KOH buffer (pH 9.7). This enzyme solution was dialyzed against a buffer of the same composition, the precipitate formed during dialysis was removed by filtration, the resulting solution of the enzyme was left standing at a low temperature, and thus the s-AST-inactivating enzyme was obtained in crystalline form.

Table 2 shows AST isozyme inhibitory activities of the enzyme, protein quantities (expressed in absorbance at 280 nm), specific activities (inhibitory activity/protein quantity), and yields of the enzyme, through the above-mentioned purification steps.

TABLE 2

| Step | Volume (ml) | Inhibitory activity (unit) | Protein (OD) | Specific activity | Yield (%) |
| --- | --- | --- | --- | --- | --- |
| Filtrate of culture broth | 17,500 | 655,000 | 330,000 | 2.0 | 100 |
| Precipitation with (NH$_4$)$_2$SO$_4$ | 1,000 | 555.000 | 18,000 | 30.8 | 85 |
| SP-Sephadex | 500 | 424,000 | 1,500 | 283 | 64.7 |
| DEAE-Sephadex | 320 | 372,000 | 1,040 | 359 | 56.8 |
| Crystallization | 10 | 77,000 | 188 | 410 | 11.8 |

What is claimed is:

1. A process for preparing an enzyme capable of inactivating cytosolic aspartate aminotransferase isozyme which comprises cultivating a strain of *Streptomyces violaceochromogenes* strain No. 9722 (FERM BP-646) under operating conditions effective to produce and accumulate recoverable amounts of said enzyme and recovering said enzyme from the culture.

* * * * *